United States Patent
Chin et al.

(10) Patent No.: US 6,899,672 B2
(45) Date of Patent: May 31, 2005

(54) ENDOSCOPIC IMAGING SYSTEM INCLUDING REMOVABLE DEFLECTION DEVICE

(75) Inventors: Yem Chin, Burlington, MA (US); Louis J. Barbato, Franklin, MA (US); Michael S. Banik, Bolton, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 142 days.

(21) Appl. No.: 10/291,889

(22) Filed: Nov. 8, 2002

(65) Prior Publication Data

US 2004/0092794 A1 May 13, 2004

(51) Int. Cl.$^7$ ................................................ A61B 1/00
(52) U.S. Cl. ...................... 600/121; 600/123; 600/143
(58) Field of Search ................................. 600/121, 123, 600/133, 139, 143, 144, 146, 152, 153

(56) References Cited

U.S. PATENT DOCUMENTS

| | | | | |
|---|---|---|---|---|
| 4,798,193 A | * | 1/1989 | Giesy et al. | ................ 600/114 |
| 4,893,613 A | * | 1/1990 | Hake | .......................... 600/152 |
| 5,025,778 A | * | 6/1991 | Silverstein et al. | ......... 600/104 |
| 5,363,135 A | | 11/1994 | Inglese | |
| 5,860,914 A | * | 1/1999 | Chiba et al. | ................. 600/151 |
| 5,921,915 A | * | 7/1999 | Aznoian et al. | ............ 600/104 |
| 6,174,280 B1 | * | 1/2001 | Oneda et al. | ................ 600/121 |
| 6,585,641 B1 | * | 7/2003 | Jordfald | ....................... 600/144 |
| 2002/0107478 A1 | | 8/2002 | Wendlandt | |

* cited by examiner

Primary Examiner—Beverly M. Flanagan
(74) Attorney, Agent, or Firm—Christensen O'Connor Johnson Kindness PLLC

(57) ABSTRACT

A steerable endoscopic sheath has a proximal end, a distal end and a working channel lumen disposed therein. A plurality of solid state light emitting devices such as light emitting diodes are positioned near the distal end of the sheath and are selectively energized to illuminate internal body tissues. An imaging device such as a photo diode or CCD array creates an image from light reflected from the tissue. The distal tip of the endoscopic sheath is selectively moveable with a deflection device that is insertable into the sheath. The deflection device includes a tip deflection mechanism that allows a user to move the tip of the deflection device. With the deflection device inserted in the sheath, movement of the distal tip causes a corresponding movement in the distal tip of the sheath. The distal tip of the sheath has a shape retaining mechanism that allows it to retain the shape imparted by the deflection device once the deflection device is removed from the sheath.

12 Claims, 5 Drawing Sheets

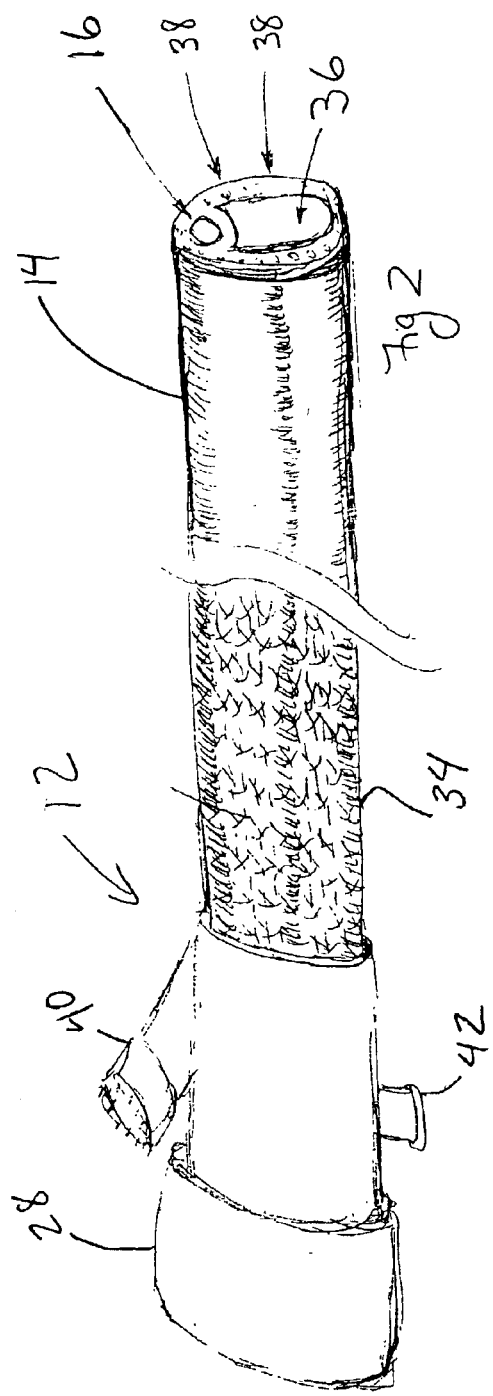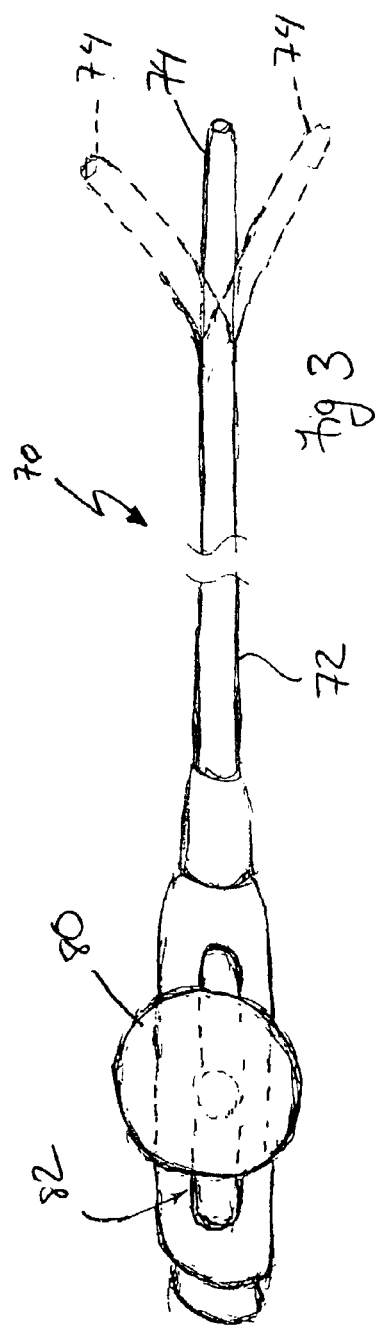

ENDOSCOPIC IMAGING SYSTEM INCLUDING REMOVABLE DEFLECTION DEVICE

FIELD OF THE INVENTION

The present invention relates to medical devices and in particular to imaging endoscopes.

BACKGROUND OF THE INVENTION

Most minimally invasive surgical procedures performed in the GI tract or other internal body cavities are accomplished with the aid of an endoscope. A typical endoscope has an illumination channel and an imaging channel both of which are made of a bundle of optical fibers. The illumination channel is coupled to a light source to illuminate an internal body cavity of a patient and the imaging channel transmits an image created by a lens at the distal end of the scope to a connected camera unit or display device. Most endoscopes also have a working channel through which an elongated treatment/surgical device may be passed. The treatment device usually has a handle or control at its proximal end that is manipulated by a physician to perform some surgical procedure.

While endoscopes are a proven technology, most are generally costly to manufacture. In addition, the optical fibers in the endoscope are subject to breakage during handling or sterilization procedures and are costly to repair. In order to limit breakage of the optical fibers, most endoscopes are relatively stiff. Such stiffness is usually achieved by making the working channel relatively small compared to the diameter of the scope. However, a small working channel limits the size of the medical device that can be inserted into the channel. Alternatively, if the working channel is made larger, the thickness of the endoscope is increased, thereby reducing the number of locations to which the scope can be routed.

Given these shortcomings, there is a need for an endoscope that does not rely on optical fibers for transmitting light into or images out of a body cavity. In addition, the endoscope should be able to be made with a relatively small diameter without unduly narrowing the size of the working channel.

SUMMARY OF THE INVENTION

To address these and other concerns, the present invention is an endoscopic sheath having a flexible illumination and imaging mechanism. The illumination mechanism preferably includes a number of solid state light emitters such as light emitting diodes to illuminate a body cavity. The imaging mechanism includes a photo-detector or solid state camera chip, positioned at the distal end of the sheath, that produces an image of the tissue in the body cavity.

The endoscopic sheath has a distal end that is selectively positionable in the cavity by a removable deflection device. In one embodiment, the deflection device is a catheter having a steering mechanism such as one or more steering wires that extend along its length. The deflection device is inserted into the endoscopic sheath and the steering mechanism adjusted to move its distal tip. Movement of the tip of the deflection device creates a corresponding movement at the distal end of the endoscopic sheath. In one embodiment, the distal end of the endoscopic sheath has a shape retaining mechanism that maintains its desired position when the deflection device is removed.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 2 illustrates one embodiment of an endoscopic sheath in accordance with the present invention;

FIG. 3 illustrates one embodiment of a deflection device for positioning the endoscopic sheath;

FIGS. 6 and 7 illustrate different embodiments of a shape retaining mechanism in the endoscopic sheath.

DETAILED DESCRIPTION OF THE PREFERRED EMBODIMENT

Figure 1:
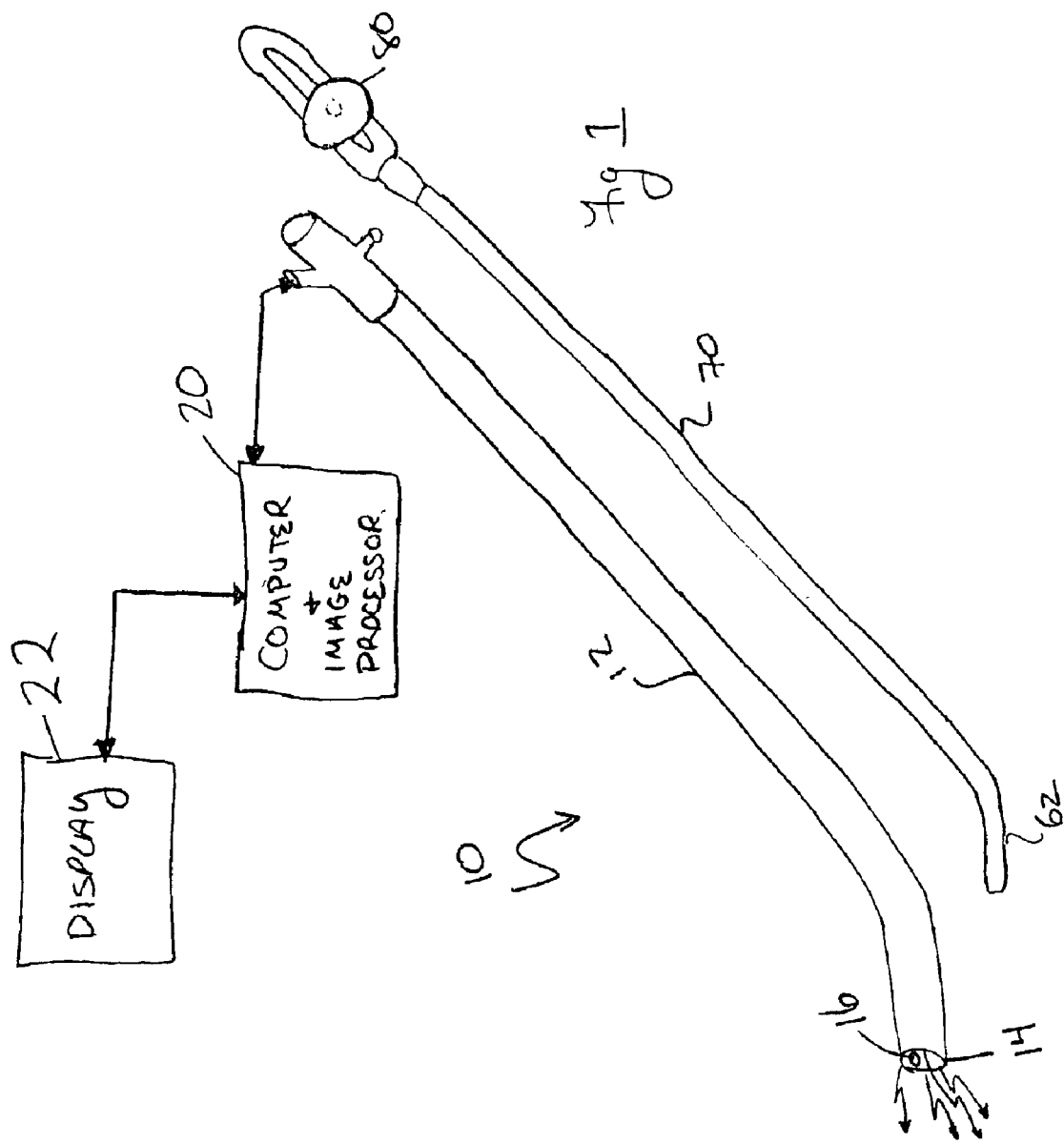
FIG. 1 shows an endoscopic imaging system in accordance with one embodiment of the present invention.

An endoscopic imaging system 10, in accordance with one embodiment of the present invention includes an endoscopic sheath 12 that emits light from its distal end 14 onto a tissue sample of interest. Light reflected from the tissue is received by an imaging device 16 at the distal end of the endoscopic sheath 12. Signals from the imaging device 16 are received by a computer and image processor 20 that is coupled to the endoscopic sheath 12. The computer and image processor 20 produces an image of the tissue that is shown to a physician on a display terminal 22.

As will be explained in further detail below, the distal end 14 of the endoscopic sheath may be oriented in a desired direction by a deflection device 70 that fits within a lumen of the endoscopic sheath 12. The deflection device 70 includes a steering mechanism, such as a number of pull wires or the like, that allow a distal end 62 of the deflection device 70 to be manipulated in a desired direction. Once the distal end 14 of the endoscopic sheath 12 has been positioned in the desired direction, the deflection device 70 is removed from the lumen in the endoscopic sheath 12. The distal end 14 of the sheath 12 has a shape retaining mechanism that retains its position even with the deflection device 70 removed.

FIG. 2 shows the endoscopic sheath 12 in accordance with one embodiment of the present invention in greater detail. The sheath 12 comprises an elongated tube having a proximal end 28, a distal region 30 that terminates at the distal end 14, and at least one lumen extending from the proximal end to the distal end that defines a working channel 36. Disposed at the distal end 14 of the endoscopic sheath 12 are a number of solid state light sources 38 such as light emitting diodes (LED's). Each LED includes a pair of flexible wires (not shown) that terminate at a connector 40 at the proximal end 28 of the endoscopic sheath 12. The light sources 38 may be clear LED's or colored LED's such as red, green and blue. White light images can be created by illuminating the clear LED's and recording an image. Alternatively, red, green and blue images can be created by sequential illumination of the tissue with the red, green and blue LED's and combining the colored images in the computer and image processor 20 or on the display 22. Light reflected from the internal body cavity is received by the imaging device 16 such as a photo-diode, solid state camera including a CCD array or other image sensor. Electronic signals representative of the illuminated tissue are carried to the computer and image processor 20 shown in FIG. 1 via wires that terminate at the connector 40 at the proximal end 28 of the endoscope. A flushing port 42 at the proximal end of the endoscopic sheath allows liquids to be delivered through the sheath in order to clear the image sensor 16 and generally flush the working channel 36.

Figure 4:
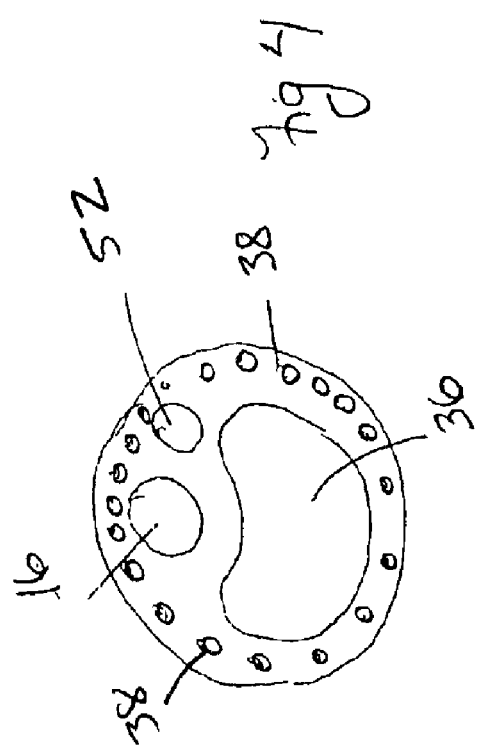
FIG. 4 illustrates a number of lumens in the endoscopic sheath.

FIG. 4 shows the distal tip 14 of the endoscopic sheath 12. The tip has a number of solid state light sources 38 disposed about the working channel 36. In addition, the sheath may include a flushing port lumen 52 through which saline or other liquids/gasses can be delivered. The flushing port lumen 52 may be designed such that a portion of the liquid/gas delivered clears the surface of the imaging device 16.

The distal region 30 of the endoscopic sheath 12 has a flexibility that is generally more flexible than the proximal end 28. The proximal end may have a braid 34 or other stiffening member embedded within the walls of the sheath. The stiffening member does not extend all the way to the distal region 30 of the sheath and therefore the distal region 30 is more flexible than the proximal end.

FIG. 3 shows one embodiment of a deflection device 70 that is inserted within a lumen of the endoscopic sheath 12 in order to position the distal tip of the sheath in the desired direction. In one embodiment of the invention, the deflection device is inserted into the working channel 36. However, other lumens could be provided in the endoscopic sheath specifically for receiving the deflection device. The deflection device 70 comprises an elongate catheter 72 having a flexible tip 74 that includes a steering mechanism such as a number of pull wires (not shown) to direct the flexible tip 74. Each pull wire is preferably positioned along an edge of the catheter 72 and has a proximal end secured to a wheel 80 within a handle at the proximal end of the deflection device. By rotating the wheel 80, two opposing pull wires are simultaneously compressed and extended on either side of the catheter thereby bending the distal tip 74 in a desired direction within a plane. In addition, the wheel 80 can be moved within a slot 82 within the handle in order to compress and extend another pair of pull wires, so that the tip moves back and forth in another plane. Although the present embodiment of the invention uses pull wires as a steering mechanism, it will be appreciated that other techniques such as fluid/air inflatable bladders, magnetic forces, electromechanical actuators, etc. could be used to bend the tip of the deflection device 70 in the desired direction.

Figure 5:
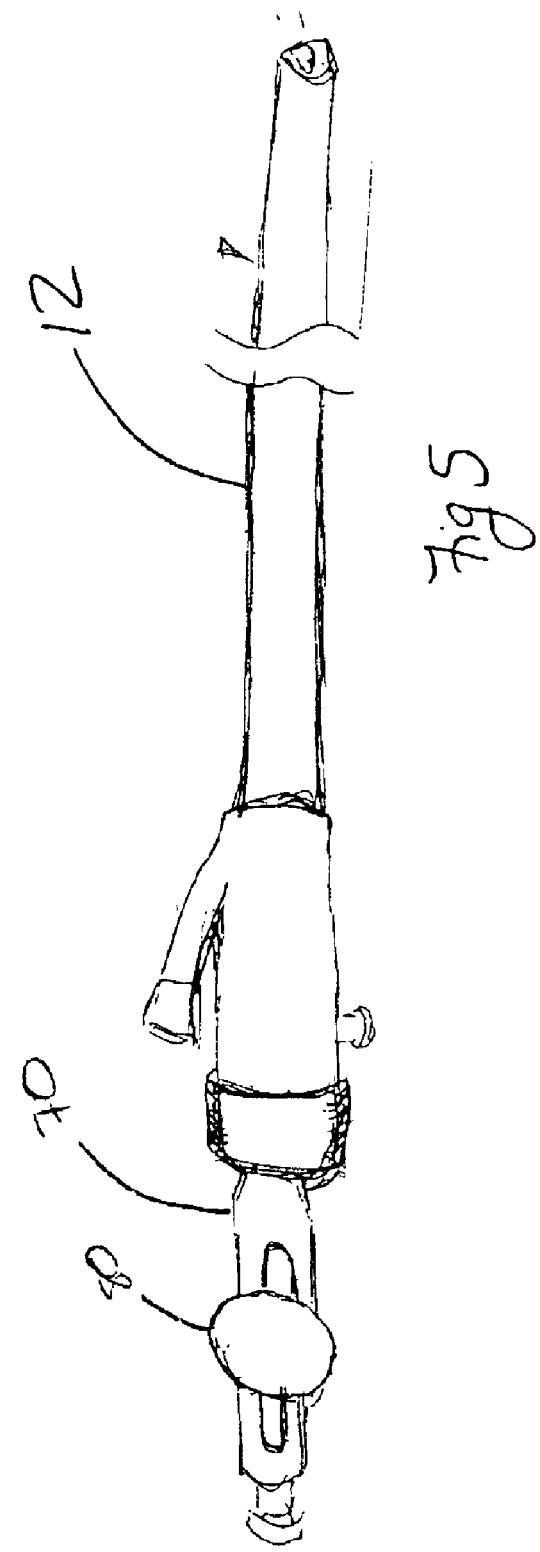
FIG. 5 illustrates the deflection device within the endoscopic sheath.
Figure 9:
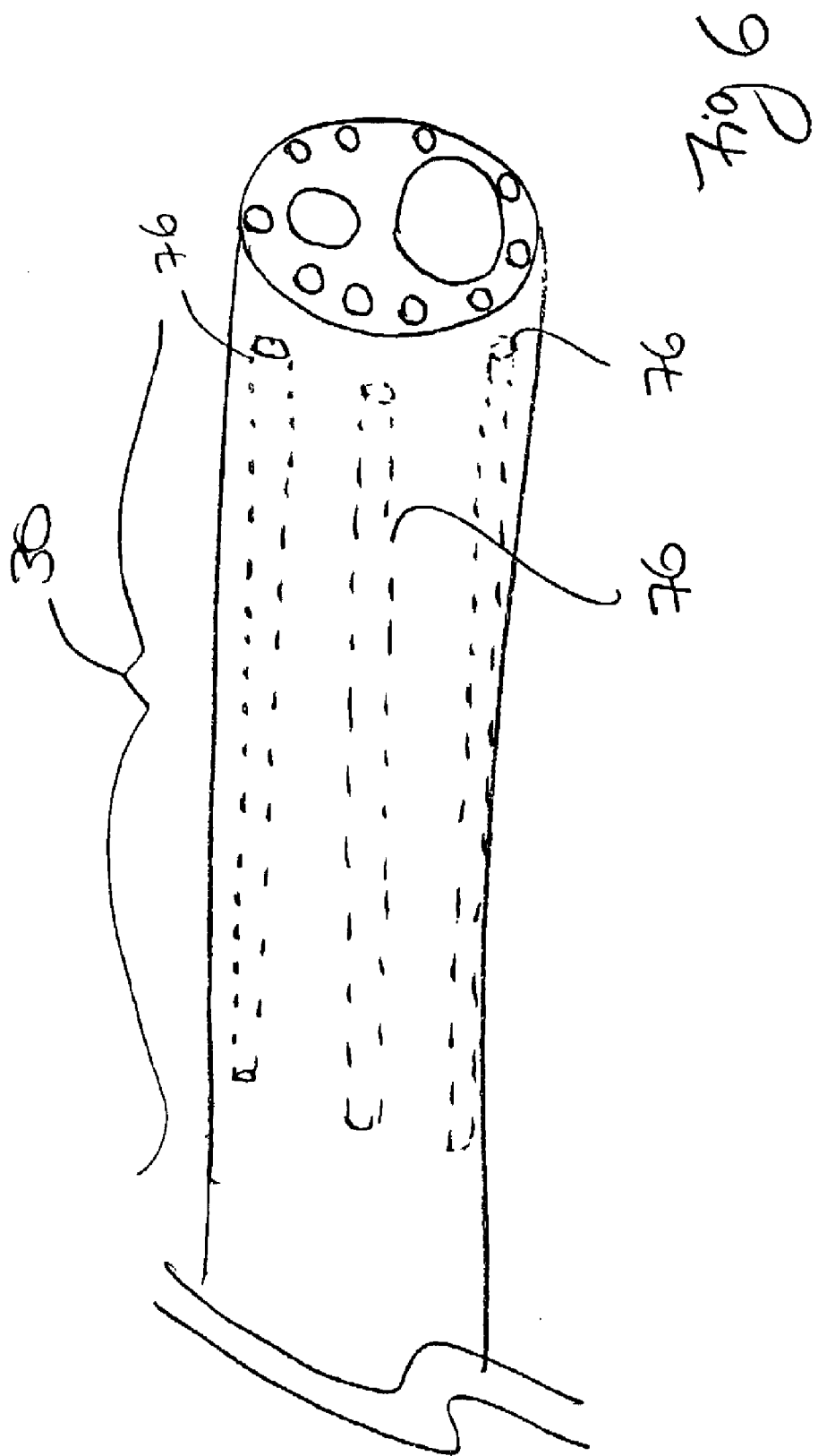

In one embodiment, the distal tip 74 of the deflection device 70 is more flexible than a proximal region of the catheter 72 thereby restricting the effect of the steering mechanism to the distal tip 74. Upon the insertion of the deflection device 70 within the working channel 36 of the endoscopic sheath 12, as shown in FIG. 5, movement of the distal tip 74 causes a corresponding movement in the distal tip 14 of the endoscopic sheath. Once the distal tip 14 of the sheath is oriented in the desired direction, the deflection device 70 is withdrawn from the lumen and the distal tip 14 of the sheath retains its desired position so that the physician can access and view a desired region of the patient's body.

As indicated above, the distal region 30 of the endoscopic sheath 12 has a shape retaining mechanism that is flexible enough to be moved by the deflection device 70 and allows the distal tip 14 of the endoscopic sheath to retain its shape once the deflection device is removed from the working channel 36.

Figure 7:
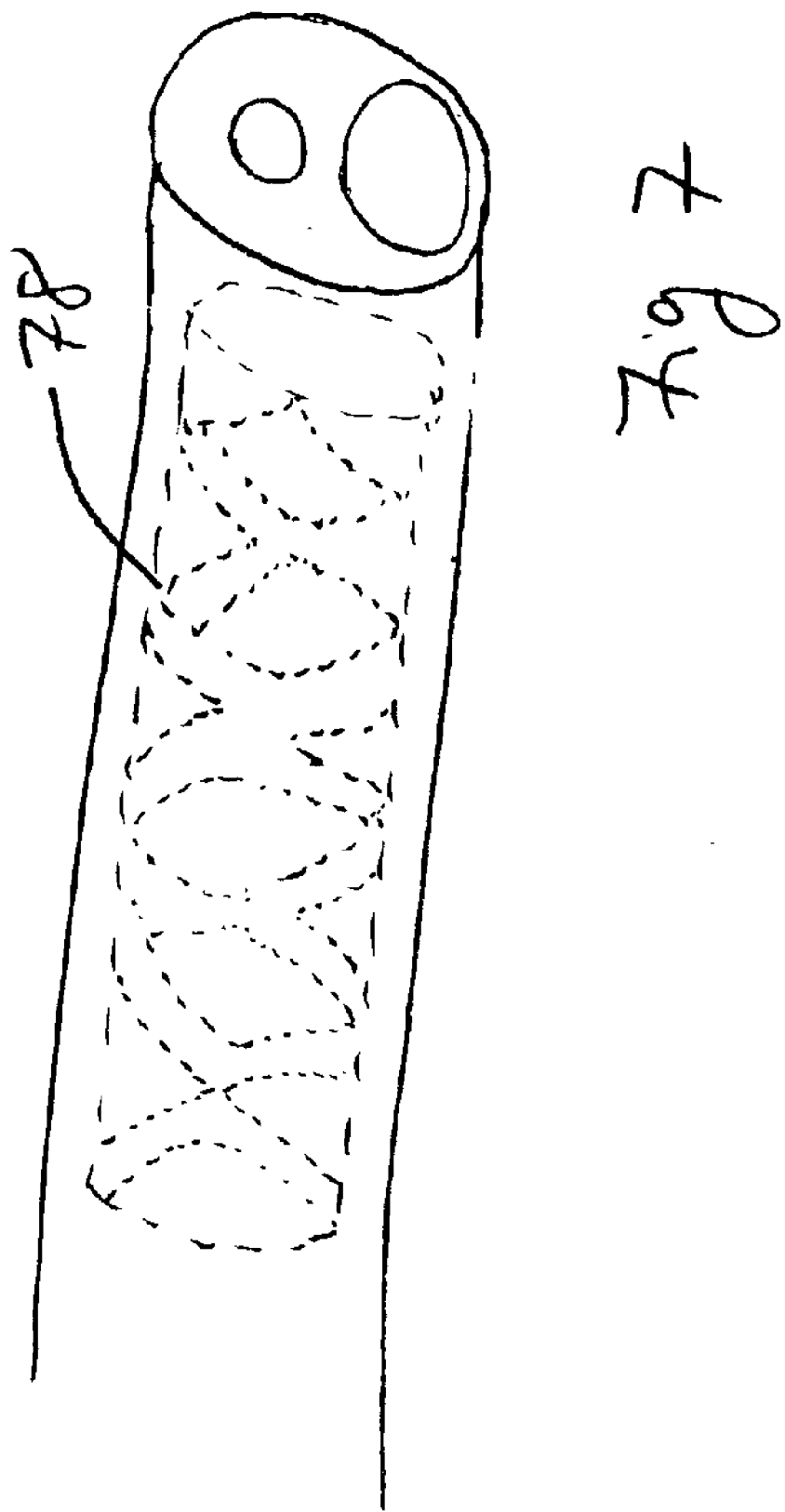

The shape retaining mechanism can be made by selecting shape retaining materials for the manufacture of the distal region 30 of the sheath. Alternatively, shape retaining mechanisms such as wires 76 can be embedded within the distal region 30 as shown in FIG. 6. The wires 76 are bent by the deflection device 70, but retain their shape when the deflection device 70 is removed. Alternatively, a braided stent 78 with a shape retaining ability can be incorporated into the distal region 30 of the sheath as shown in FIG. 7 to maintain its shape once the deflection device 70 is removed.

By allowing the endoscopic sheath 12 to be oriented in a desired direction with a removable deflection device, the sheath 12 can be made thinner than conventional endoscopes because no steering wires need be incorporated into the device. In addition, the size of the working channel can be increased relative to the size of the sheath because the sheath doesn't need to be as stiff in order to prevent breakage of optical fibers.

While the preferred embodiment of the invention has been illustrated and described, it will be appreciated that various changes can be made therein without departing from the scope of the invention. Therefore, the scope of the invention is to be determined from the following claims and equivalents thereof.

The embodiments of the invention in which an exclusive property or privilege is claimed are defined as follows:

1. An imaging endoscope, comprising:
   a shape retaining endoscopic sheath having a proximal end, a distal end and a working channel disposed therein that extends from the proximal end to the distal end;
   a light source disposed at the distal end of the sheath to illuminate internal body tissues;
   an image sensor;
   means for retaining the shape of the endoscopic sheath upon removal of a deflection device;
   a deflection device for selectively positioning the distal end of the sheath, the deflection device including:
      an elongate shaft having a proximal and a distal end and a steering mechanism for moving the distal end;
      wherein the elongate shaft fits within the working channel of the endoscope and engages the distal end of the sheath such that when the distal end of the deflection device is moved, the distal end of the sheath is also moved.

2. The imaging endoscope of claim 1, wherein the steering mechanism in the deflection device includes one or more pull wires.

3. The imaging endoscope of claim 1, wherein the distal end of the endoscopic sheath is more flexible than the proximal end.

4. The imaging endoscope of claim 3, wherein the proximal end of the endoscopic sheath includes a reinforcing braid.

5. The imaging endoscope of claim 1, wherein the image sensor includes a photo-detector.

6. The imaging endoscope of claim 1, wherein the image sensor includes a CCD array.

7. The imaging endoscope of claim 1, wherein the means for retaining the shape of the endoscopic sheath is a bendable metallic member.

8. A system for imaging internal body tissue, comprising:
   a disposable endoscopic sheath having a proximal end, a distal end, a shape retaining mechanism, a working channel extending from the proximal end to the distal end, a number of light emitting diodes at the distal end that are selectively activated to illuminate the body tissue and an image sensor for producing an image of the body tissue; and a deflection catheter having a proximal end, a distal end and one or more pull wires that move the distal end, the deflection catheter being selectively inserted into the working channel of the sheath to move the distal tip of the endoscope and removable such that the endoscopic sheath retains the shape imparted by the deflection catheter.

9. A disposable imaging endoscope, comprising:

an endoscopic sheath having a proximal end, a distal end and at least one lumen extending from the proximal end to the distal end;

a plurality of light emitting diodes at the distal end of the sheath that are selectively activated to illuminate internal body tissue;

an image sensor disposed at the distal end of the sheath that transmits electrical signals representative of an image of a tissue sample;

the distal end of the sheath further including a shape retaining mechanism that is movable by a deflection device that is insertable into the lumen, said shape retaining mechanism retaining the shape of the distal end of the sheath after the deflection device is removed from the lumen.

10. The disposable imaging endoscope of claim 9, wherein the shape retaining mechanism includes one or more wires disposed adjacent the distal tip of the sheath.

11. The disposable imaging endoscope of claim 9, wherein the shape retaining mechanism is a flexible stent adjacent the distal end of the sheath.

12. A method of capturing images from an internal body cavity of a patient, comprising:

inserting an endoscope into the patient, the endoscope having a proximal end, a distal end, a working channel, a plurality of light emitting diodes that produce light at the distal end of the endoscope and an image sensor for producing an image of the internal body cavity;

selectively positioning the distal end of the endoscope by inserting a deflection catheter into the endoscope and moving a distal tip of the deflection catheter to move the distal end of the endoscope; and withdrawing the deflection catheter from the endoscope such that the endoscope retains a position imparted by the deflection catheter.

* * * * *